(12) United States Patent
Hunsdon

(10) Patent No.: US 12,121,377 B2
(45) Date of Patent: Oct. 22, 2024

(54) LIGHT SOURCE FOR AN IMAGING SYSTEM AND METHODS OF THE SAME

(71) Applicant: Hologic, Inc., Marlborough, MA (US)

(72) Inventor: Adrian Hunsdon, Southbury, CT (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 18/468,849

(22) Filed: Sep. 18, 2023

(65) Prior Publication Data
US 2024/0148347 A1 May 9, 2024

Related U.S. Application Data

(63) Continuation of application No. 17/446,200, filed on Aug. 27, 2021, now Pat. No. 11,801,018.
(Continued)

(51) Int. Cl.
*A61B 6/04* (2006.01)
*A61B 6/40* (2024.01)
*A61B 6/50* (2024.01)

(52) U.S. Cl.
CPC .......... *A61B 6/0414* (2013.01); *A61B 6/0435* (2013.01); *A61B 6/40* (2013.01); *A61B 6/502* (2013.01)

(58) Field of Classification Search
CPC ........... A61B 1/00; A61B 1/06; A61B 1/0605; A61B 1/0653; A61B 1/0655; A61B 6/50; A61B 6/502; A61B 6/0414; A61B 6/0421; A61B 6/025; A61B 6/5035; A61B 6/03; A61B 5/0091; A61B 5/4312; A61B 5/708
See application file for complete search history.

(56) References Cited

U.S. PATENT DOCUMENTS

| 5,068,887 | A | 11/1991 | Hughes |
| 7,792,245 | B2 | 9/2010 | Hitzke |

(Continued)

FOREIGN PATENT DOCUMENTS

| CN | 102196772 A | 9/2011 |
| CN | 202665567 U | 1/2013 |

(Continued)

OTHER PUBLICATIONS

European Extended Search Report in Application 21198811.8, mailed Feb. 17, 2022, 10 pages.
(Continued)

*Primary Examiner* — Don K Wong
(74) *Attorney, Agent, or Firm* — Merchant & Gould P.C.

(57) ABSTRACT

An imaging system includes a gantry and a compression system coupled to the gantry and rotatable relative to the gantry. The compression system includes a compression paddle, a support platform, and an x-ray receptor disposed below the support platform. An x-ray tube head is coupled to the gantry and includes an x-ray source and a light source. The x-ray tube head is independently rotatable relative to the gantry and the compression system. The light source is configured to generate at least a first light type and a different second light type directed towards the support platform. The second light type being mapped to an x-ray field of the x-ray source, and the generated second light type is based on a tilt angle of the x-ray tube head relative to the support platform and a compression force of the compression paddle.

20 Claims, 9 Drawing Sheets

Related U.S. Application Data

(60) Provisional application No. 63/198,015, filed on Sep. 24, 2020.

(56) References Cited

U.S. PATENT DOCUMENTS

| | | |
|---|---|---|
| 8,611,491 B2 | 12/2013 | Holler et al. |
| 11,801,015 B2 | 10/2023 | Hunsdon |
| 2007/0036265 A1 | 2/2007 | Jing |
| 2007/0139799 A1 | 6/2007 | Ramsauer |
| 2009/0323892 A1 | 12/2009 | Hitzke et al. |
| 2014/0294142 A1 | 10/2014 | Choi |
| 2021/0401381 A1 | 12/2021 | Wells |

FOREIGN PATENT DOCUMENTS

| | | | | |
|---|---|---|---|---|
| CN | 103402431 A | 11/2013 | | |
| CN | 107106100 A | 8/2017 | | |
| EP | 3692921 | 8/2020 | | |
| JP | 2008-023015 A | 2/2008 | | |
| JP | 2012-019842 | 2/2012 | | |
| JP | 2012-050519 | 3/2012 | | |
| JP | 2015-178010 | 10/2015 | | |
| JP | 2022-502138 | 1/2022 | | |
| KR | 20160059943 A | * | 5/2016 | ............ G01N 23/02 |
| WO | 2006061357 | 6/2006 | | |
| WO | 2017/056533 | 4/2017 | | |
| WO | 2020/069031 | 4/2020 | | |

OTHER PUBLICATIONS

Zimmerman, B. et al., "A novel tomographic optical breast imaging system to simultaneously co-register x-ray tomosynthesis", Biomedical Optics, 1-3 (Jan. 2014).

* cited by examiner

LIGHT SOURCE FOR AN IMAGING SYSTEM AND METHODS OF THE SAME

CROSS-REFERENCE TO RELATED APPLICATIONS

This application is a continuation of U.S. patent application Ser. No. 17/446,200, filed Aug. 27, 2021, now U.S. Pat. No. 11,801,018, which claims priority to, and the benefit of, U.S. Provisional Patent Application No. 63/198,015, filed Sep. 24, 2020, the disclosures of which are hereby incorporated by reference herein in their entireties.

BACKGROUND

Compression during mammography and tomosynthesis imaging serves a number of purposes. For example, it: (1) makes the breast thinner in the direction of x-ray flux and thereby reduces patient radiation exposure from the level required to image the thicker parts of a breast that are not compressed; (2) makes the breast more uniform in thickness in the direction of x-ray flux and thereby facilitates more uniform exposure at the image plane over the entire breast image; (3) immobilizes the breast during the x-ray exposure and thereby reduces image blurring; and (4) brings breast tissues out from the chest wall into the imaging exposure field and thus allows for more tissue imaging. As the breast is being compressed, typically a technologist manipulates the breast to position it appropriately and counter the tendency that compression has of pushing breast tissue toward the chest wall and out of the image field.

Standard compression methods for mammography and tomosynthesis use a movable, rigid, radiolucent compression paddle. The breast is placed in an imaging area on a breast support platform that typically is flat, and the paddle then compresses the breast, usually while a technologist or other health professional is holding the breast in place. The technologist may also manipulate the breast to ensure proper tissue coverage in the image receptor's field of view.

At least some known x-ray tube heads have a headlamp that generates a light directed towards a breast support platform. This light illuminates the support platform and the area above the platform to aid the technologist in positioning the patient's breast prior to compression. Additionally, this light is also used as a visual mapping indicator of an x-ray field so that the technologist can confirm the positioning of the patient's breast prior to image acquisition. However, as the x-ray tube head tilts relative to the support platform, the accuracy of the visual mapping indicator decreases and no longer reflects the expected x-ray field because of the angle of the tube head.

SUMMARY

In one aspect, the technology relates to an imaging system including: a gantry; a compression system coupled to the gantry and rotatable relative to the gantry, wherein the compression system includes a compression paddle, a support platform, and an x-ray receptor disposed below the support platform; and an x-ray tube head coupled to the gantry and including an x-ray source and a light source, wherein the x-ray tube head is independently rotatable relative to the gantry and the compression system, wherein the light source is configured to generate at least a first light type and a different second light type directed towards the support platform, the second light type being mapped to an x-ray field of the x-ray source, and wherein the generated second light type is based on a tilt angle of the x-ray tube head relative to the support platform and a compression force of the compression paddle.

In an example, when the tilt angle of the x-ray tube head is greater than or equal to a predetermined value or the compression force of the compression paddle is less than or equal to a predetermined value, the light source generates the first light type. In another example, the light source is a multi-colored light emitting diode. In yet another example, the first light type is a different color than the second light type. In still another example, the first light type is a white light.

In another aspect, the technology relates to a method of illuminating a support platform of an imaging system, the imaging system including: (a) a gantry, (b) a compression system including a compression paddle, the support platform, and an x-ray receptor disposed below the support platform, the compression system rotatable relative to the gantry, and (c) an x-ray tube head including a light source and independently rotatable relative to the gantry and the compression system, the method including: generating, via the light source, a first light type directed towards the support platform; determining a tilt angle of the x-ray tube head; determining a compression force of the compression paddle; and changing the first light type to a second light type generated by the light source based on the determined tilt angle and the determined compression force, wherein the first light type is different than the second light type.

In an example, the method further includes reverting to the first light type by the light source based on a change in either the determined tilt angle or the determined compression force. In another example, determining the tilt angle of the x-ray tube head includes measuring the tilt angle relative to the support platform, and comparing the measured tilt angle to a predetermined value. In yet another example, when the measured tilt angle is less than or equal to the predetermined value, the first light type is changeable to the second light type, and when the measured tilt angle is greater than the predetermined value, the second light type changes to the first light type. In still another example, the predetermined value is between about 0° to ±10°. In an example, determining the compression force includes measuring the compression force applied by the compression paddle to a patient's breast, and comparing the measured compression force to a predetermined value.

In another example, when the measured compression force is less than or equal to the predetermined value, the first light type is changeable to the second light type, and when the measured compression force is greater than the predetermined value, the second light type changes to the first light type. In yet another example, the predetermined value is between about 0 to 5 pounds. In still another example, the first light type is a different color than the second light type. In an example, the first light type is a white light. In another example, the second light type maps to an x-ray field of an x-ray source of the x-ray tube head.

In another aspect, the technology relates to a method of illuminating a support platform of an imaging system, the imaging system including: (a) a gantry, (b) a compression system including a compression paddle, the support platform, and an x-ray receptor disposed below the support platform, the compression system rotatable relative to the gantry, and (c) an x-ray tube head including an x-ray source and a light source and independently rotatable relative to the gantry and the compression system, the method including: generating, via the light source, a mapping light directed towards the support platform, wherein the mapping light is based on the x-ray tube head being at a substantially orthogonal position relative to the support platform and the compression paddle generating a compression force on a patient's breast, and wherein the mapping light corresponds to an x-ray field of the x-ray source; monitoring a tilt angle of the x-ray tube head relative to the support platform; monitoring the compression force of the compression paddle; and changing the mapping light generated by the light source to a working light generated by the light source based on the tilt angle of the x-ray tube moving away from the substantially orthogonal position or the compression force being less than or equal to a predetermined value.

In an example, the mapping light is a different color than the working light. In another example, the working light is a white light. In yet another example, the method further includes adjusting the intensity of the working light.

In another aspect, the technology relates to a method of compressing a patient's breast on an imaging system, the imaging system including: (a) a gantry, (b) a compression system including a compression paddle, the support platform, and an x-ray receptor disposed below the support platform, the compression system rotatable relative to the gantry, and (c) an x-ray tube head including an x-ray source and a light source and independently rotatable relative to the gantry and the compression system, the method including: generating a working light directed towards the support platform via the light source; compressing the patient's breast between the compression paddle and the support platform, wherein the compression paddle induces a compression force on the patient's breast for immobilization; after compression, positioning the x-ray tube head relative to the support platform such that the x-ray tube head is substantially orthogonal to the support platform; changing the working light generated by the light source to a mapping light generated by the light source based on the position of the x-ray tube head and the compression force of the compression paddle; and verifying the patient's breast is located within an x-ray field of the x-ray source via the mapping light.

In an example, the method further including after the working light is changed to the mapping light, releasing the patient's breast from compression and automatically reverting to the working light. In an example, the method further including after the working light is changed to the mapping light, tilting the x-ray tube head away from the substantially orthogonal position and automatically reverting to the working light.

DETAILED DESCRIPTION

Figure 1A:
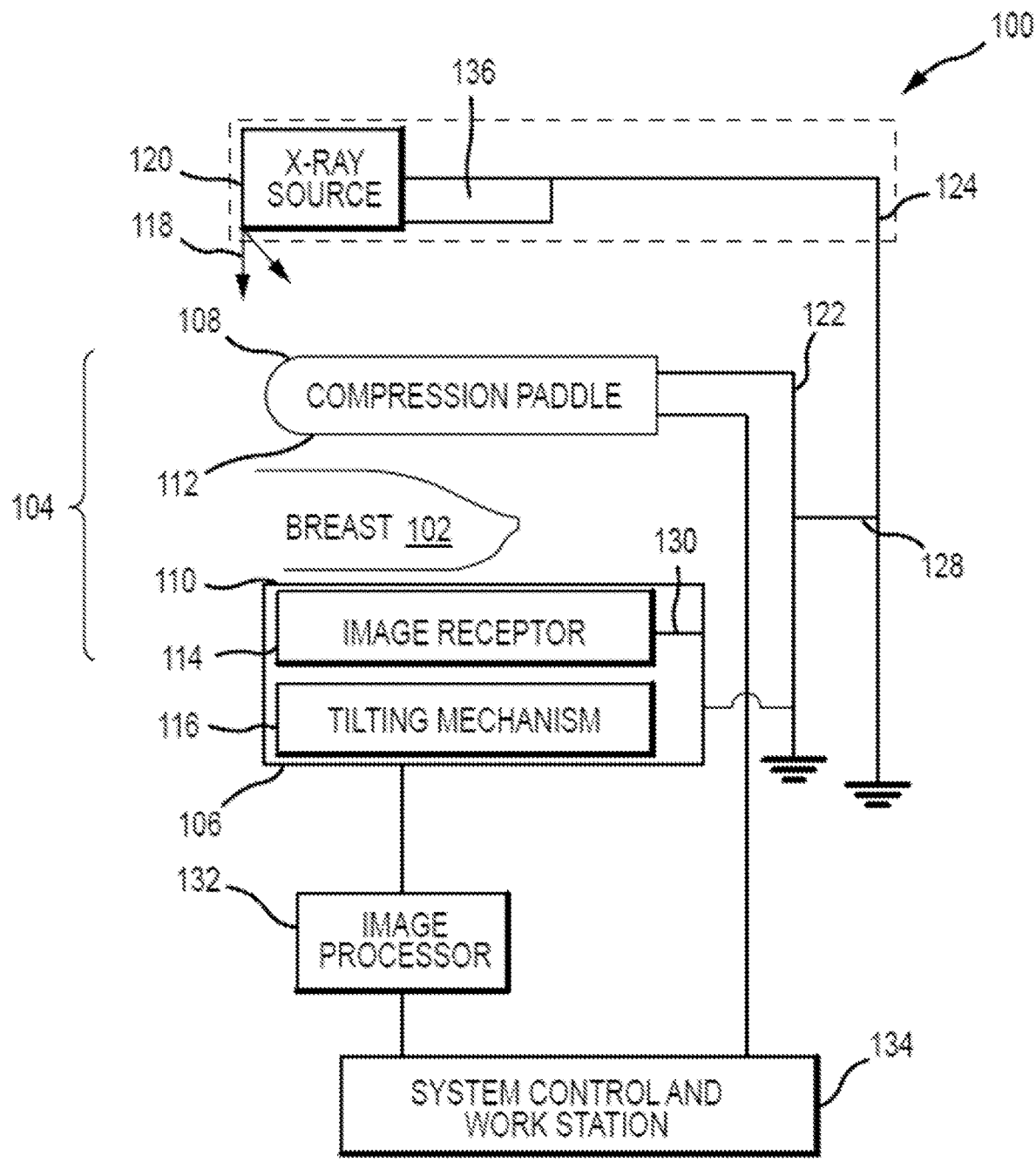
FIG. 1A is a schematic view of an exemplary imaging system.
Figure 1B:
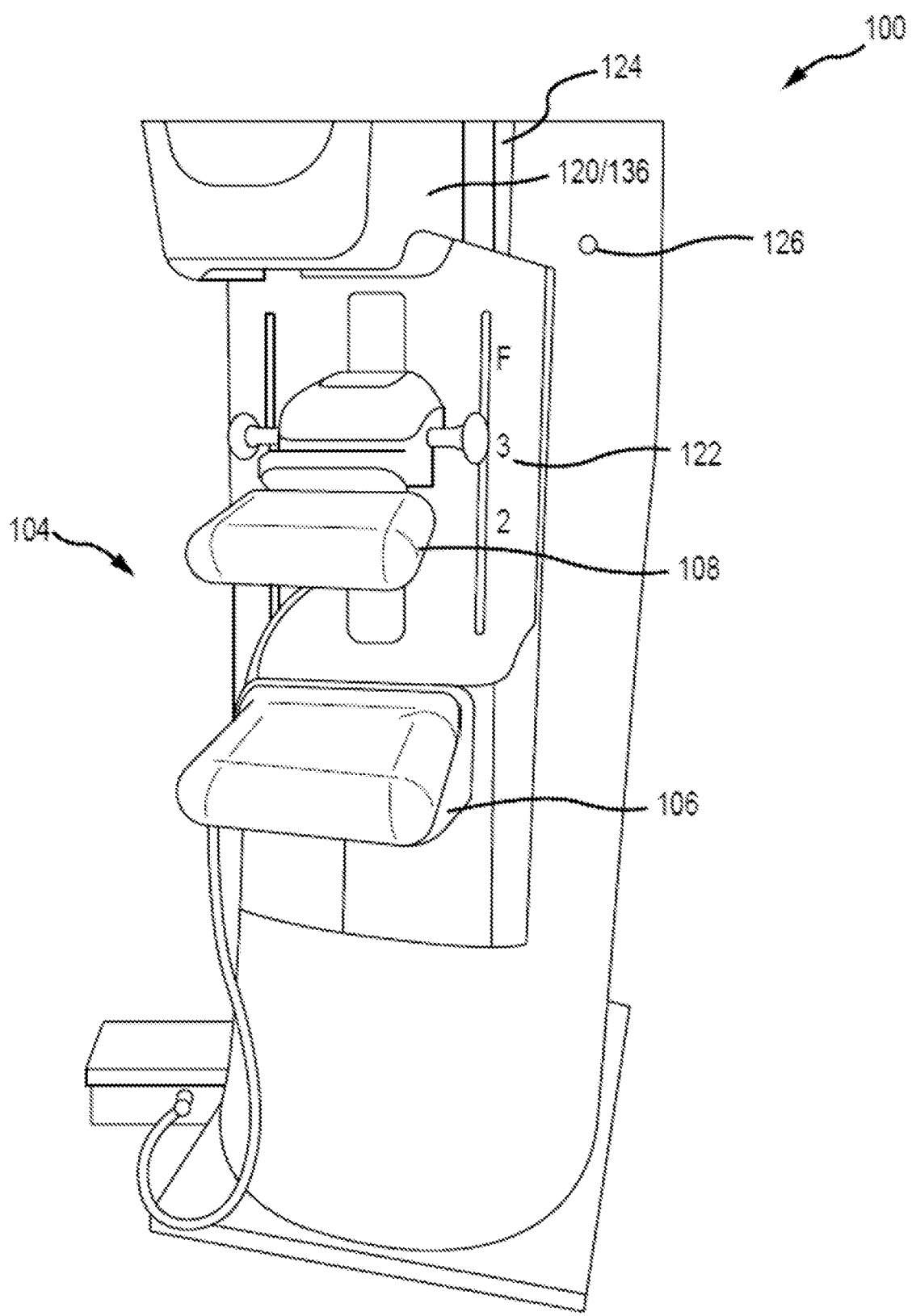
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 is configured to immobilize a patient's breast 102 for x-ray imaging (either or both of mammography and tomosynthesis) via a breast compression immobilizer unit or compression system 104. In the example, the compression system 104 includes a static breast support platform 106 and a moveable compression paddle 108. The breast support platform 106 and the compression paddle 108 each have a compression surface 110 and 112, respectively, with the compression surface 112 configured to move towards the support platform 106 to compress and immobilize the breast 102. In known systems, the compression surfaces 110, 112 are exposed so as to directly contact the breast 102. The support platform 106 also houses an x-ray image receptor 114 and, optionally, a tilting mechanism 116. The immobilizer unit 104 is in a path of an imaging x-ray beam 118 emanating from an x-ray source 120, such that the beam 118 impinges on the image receptor 114.

The compression system 104 is supported on a first support arm 122 and the x-ray source 120 is supported on a second support arm, also referred to as an x-ray tube head 124. The support arms 122, 124 are mounted on a gantry 126. For mammography, support arms 122 and 124 can rotate as a unit about an axis 128 between different imaging orientations such as cranial-caudal (CC) and mediolateral oblique (MLO) views, so that the imaging system 100 can take a mammogram projection image at each orientation. In operation, the image receptor 114 remains in place relative to the support platform 106 while an image is taken. The immobilizer unit 104 releases the breast 102 for movement of support arms 122, 124 to a different imaging orientation. For tomosynthesis, the support arm 122 stays in place, with the breast 102 immobilized and remaining in place, while at least the tube arm 124 rotates the x-ray source 120 relative to the immobilizer unit 104 and the compressed breast 102 about the axis 128. The imaging system 100 takes plural tomosynthesis projection images of the breast 102 at respective angles of the x-ray beam 118 relative to the breast 102. As such, the compression system 104 and tube head 124 may be rotated discrete from each other, unless matched rotation is required or desired for an imaging procedure.

Concurrently and optionally, the image receptor 114 may be tilted relative to the breast support platform 106 and coordinated with the rotation of the second support arm 124. The tilting can be through the same angle as the rotation of the x-ray source 120 but may also be through a different angle selected such that the x-ray beam 118 remains substantially in the same position on the image receptor 114 for each of the plural images. The tilting can be about an axis 130, which can but need not be in the image plane of the image receptor 114. The tilting mechanism 116 that is coupled to the image receptor 114 can drive the image receptor 114 in a tilting motion. For tomosynthesis imaging and/or CT imaging, the breast support platform 106 can be horizontal or can be at an angle to the horizontal, e.g., at an orientation similar to that for conventional MLO imaging in mammography. The imaging system 100 can be solely a mammography system, a CT system, or solely a tomosynthesis system, or a "combo" system that can perform multiple forms of imaging. One example of such a combo system has been offered by the assignee hereof under the trade name Selenia Dimensions.

When the system is operated, the image receptor 114 produces imaging information in response to illumination by the imaging x-ray beam 118 and supplies it to an image processor 132 for processing and generating breast x-ray images. A system control and work station unit 134 including software controls the operation of the system and interacts with the operator to receive commands and deliver information including processed-ray images.

One challenge with the imaging system 100 is how to efficiently position and compress the breast 102 on the support platform 106 such that the patient's breast 102 is immobilized for the desired or required imaging. For example, a health professional, typically an x-ray technologist, generally places the breast 102 on the support platform 106. The technologist will adjust the position of the breast 102 within the immobilizer unit 104 while pulling tissue towards the imaging area and moving the compression paddle 108 toward the breast support platform 106 to immobilize the breast 102 and keep it in place, and with as much of the breast tissue as practicable being between the compression surfaces 110, 112. However, if the patient's breast is not properly positioned within the imaging area of the imaging system 100, then the breast position and compression procedures may be required to be redone, thus increasing patient discomfort and anxiety. Additionally, an improperly positioned breast may require an x-ray image to be retaken, which then may deliver an unnecessary x-ray dose. Furthermore, once the patient's breast is immobilized on the imaging system 100, the patient (e.g., hair, arms, etc.) also needs to be positioned by the technologist out of the path (e.g., the x-ray field) of the x-ray source 120.

The technologies described herein relate to a breast compression and imaging system that utilizes light differentiation to indicate whether the light source is generating a general working light or an x-ray field mapping light. This light differentiation provides the technologist a visual aid for determining the functionality of the light being directed towards the breast support platform from the x-ray tube head. The general working light generates general illumination of the compression system, which aids the technologist when working with the patient and the imaging system. By illuminating the working area, the technologist can more efficiently position and immobilize the patient, which increases overall patient comfort. In contrast, the mapping light uses the emitted light to indicate the x-ray field of the x-ray source. The mapping light enables the technologist to more efficiently confirm that the subsequent x-ray acquisitions will adequately capture the patient's breast, which increases the overall efficiency of the imaging procedures. These technologies generally improve the accuracy of breast placement and/or compression, enabling the technologist to more efficiently ensure proper immobilization and subsequent imaging.

As described herein, the technologies utilize a light source on the x-ray tube head that is configured to change colors. In an aspect, based on a tilt angle of the x-ray tube head and a compression force generated by the compression paddle, the light source can change between the working light and the mapping light. By monitoring x-ray tube head angle and compression force of the compression paddle, the imaging system ensures that the patient is immobilized and that the light source is able to accurately correspond to the x-ray field before generating the mapping light. This ensures that the mapping light is generated only when it is accurate for the technologist to use. When either the tilt angle or the compression force changes, the imaging system automatically reverts back to the working light. Other imaging system conditions besides tilt angle and compression force are also contemplated herein. By differentiating the functionality of the light type by color, the technologist is aided when working around the compression system 104. In an aspect, the light source may be a multi-colored (e.g., RGB) light emitting diode. Additionally, the imaging system 100 includes one or more sensors that monitor the conditions of the components of the imaging system.

Imaging systems 100 including the light source that performs any one of the differentiating functions described herein are contemplated, although certain imaging systems may include all of the described imaging modalities, less than the described imaging modalities, or additional imaging modalities as required or desired.

Returning to FIG. 1A, the imaging system 100 is typically disposed within a patient room that is dimly lit to increase patient comfort and reduce patient apprehension. As such, a light source 136 is disposed within the x-ray tube head 124 so that light is provided for the system 100 and to aid the technologist with positioning and imaging the patient's breast 102 immobilized within the compression system 104. The light source 136 generally points in a downward direction towards the compression paddle 108, the breast 102, and the support platform 106. In addition, the light source 136 is configured to not interfere with the x-ray source 120 and the x-ray beams 118 during the imaging procedures. Functions performed in conjunction with the light source 136 are described herein and include generating a general working light for the compression system 104 that is configured to illuminate the support platform 106 and the area above the support platform 106 to assist the technologist with patient breast 102 positioning and presentation during compression. Additionally, the light source 136 can generate a mapping light that is configured to identify the x-ray field on the support platform 106, and so that the technologist can have confirmation that the patient breast 102 is properly positioned within the compression system 104 for x-ray image acquisition.

As used herein, the term "working light" is a light that may not necessary be shaped to correspond and identify the x-ray field of the x-ray beam 118, and as such, the technologist should not use the working light to confirm that the patient's breast 102 is properly positioned within the x-ray field. Reliance on the working light for confirming breast positioning may result in needing to reimage the patient's breast 102 due to error in breast positioning. The term "mapping light," however, is a light that is shaped to correspond and identify the x-ray field, and as such, the technologist can rely on the mapping light to confirm that the patient's breast 102 is properly positioned within the compression system 104. Reliance on the mapping light for confirming breast positioning will not result in needing to reimage the patient's breast 102 due to position error. With both the working light and the mapping light being visible light, both light types provide general illumination to the compression system 104 for the technologist.

Some standards require that for a light to be considered a mapping light, it must be correlated to the x-ray field and be within 2%. However, when the x-ray tube head 124 moves or tilts away from a substantially orthogonal position relative to the support platform 106 (e.g., as illustrated in FIG. 1B), the accuracy of the mapping light relative to the x-ray field decreases. This is because the x-ray source 120 is disposed above a collimator opening (not shown) on the tube head 124 and has a focal point that is oriented through the opening and directly towards the support platform 106. The x-ray beam 118 emanating from the source 120 can be collimated by a collimator (not shown) adjacent to the opening to account for the tilt position of the tube head 124 relative to the support platform 106. The light source 136 also uses the same tube head collimator opening to project light beams towards the support platform 106. However, the light source 136 utilizes one or more mirrors (not shown) to direct the light beams through the opening. These mirrors used by the light source 136 make it difficult to account for a tilt angle of the x-ray tube head 124. For example, when the tube head 124 is rotated, the light beams are distorted due to the keystone effect. The keystone effect can distort a substantially square shape of the light projected onto the support platform 106 into a trapezoid shape. As the distance from the edge of the tube head opening from the support platform 106 increases due to rotation, the light expands, and the tube head opening is no longer shown as a regular rectangle. Rather it is shown as more of a polygon or trapezoid shape where the edge towards the tube is shorter than the opposite edge away from the tube. As such, when the x-ray tube head 124 is directly over the support platform 106, the light beam can accurately map to the x-ray field and be within the required or desired standard, but when the x-ray tube head 124 is tilted away from the orthogonal position, the light beam is reduced in its mapping accuracy and is outside of the required or desired standard.

Figure 2:
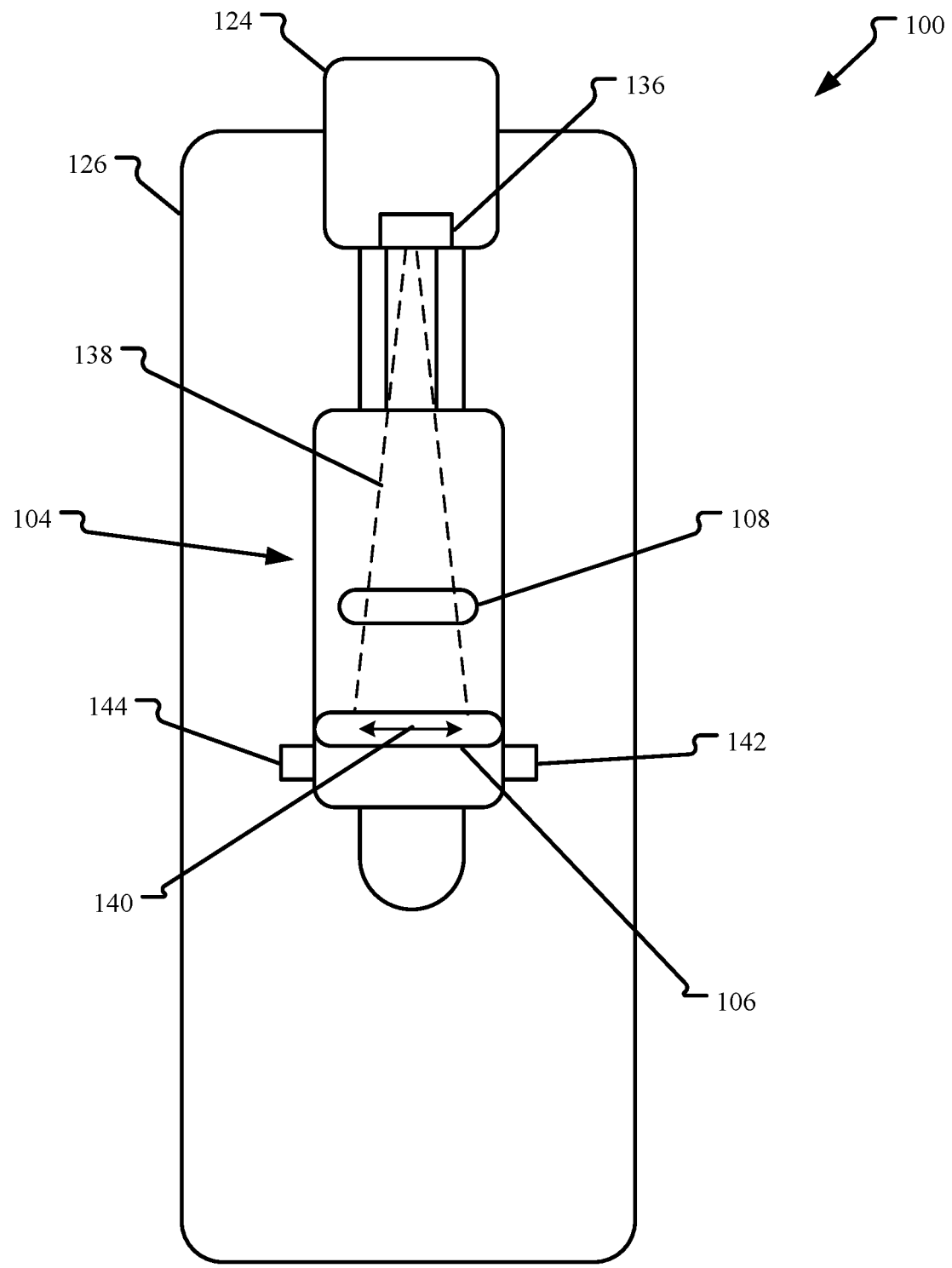
FIG. 2 is a schematic view of an exemplary light source of the imaging system shown in FIGS. 1A and 1B and with an x-ray tube head in a first position.

As used herein, the substantially orthogonal position of the x-ray tube head 124 is considered a zero degree position relative to the support platform 106 and is the position whereby the x-ray source 120 is above the support platform 106 and the path of the x-ray beam 118 is substantially orthogonal to the support platform 106. An example of this orthogonal position of the x-ray tube head 124 is illustrated in FIG. 2. It should be appreciated that because the x-ray tube head 124 and the compression system 104 can rotate as a unit (e.g., for an MLO imaging procedure), the substantially orthogonal position of the x-ray tube head 124 is not necessary in reference to the gantry 126 that supports the x-ray tube head 124. Additionally, the x-ray tube head 124 can move or tilt for any number of reasons. For example, the x-ray tube head 124 may rotate for tomosynthesis imaging procedures. In other examples, the technologist may rotate the x-ray tube head 124 while positioning the patient's breast 102 and so that the tube head 124 will not act as an impediment.

In the example, because some positions of the x-ray tube head 124 can generate inaccurate mapping lights, the light source 136 described herein is configured to distinguish the usage of the generated light (e.g., between a working light and a mapping light) and provide a visual indicator to the technologist during positioning and compression procedures. In an aspect, the light source 136 may generate different colors for the working and mapping lights and can automatically change between the two light types depending on one or more conditions of the imaging system 100. For example, based on a tilt angle of the x-ray tube head 124 and a compression force generated by the compression paddle 108, the light source 136 changes to provide the mapping light. Once the tilt angle or the compression force changes, the light source 136 can change back to the general working light. By increasing the technologist's efficiency in properly positioning and compressing the patient's breast, patient comfort during the imaging procedure is increased and anxiety is reduced.

FIG. 2 is a schematic view of the light source 136 of the imaging system 100 and with the x-ray tube head 124 in a first position. The first position is when the x-ray tube head 124 is substantially orthogonal to the support platform 106 and is at the zero-degree position. In this first position, the light source 136 generates a light 138 directed towards the support platform 106. In certain aspects, the light 138 is a general working light. Additionally, because of the position of the x-ray tube head 124, and thus the light source 136, relative to the support platform 106, the light 138 can also be configured to map to an imaging area 140 that corresponds to the x-ray field of the x-ray beam. This mapping allows the technologist to visualize the x-ray field of the x-ray beam and confirm breast placement prior to image acquisition.

In the example, the light source 136 is a light emitting diode (LED) light that is configured to emit at least two different types of light 138. These different types of light 138 correspond to either the working light or the mapping light and are used by the technologist as a visual indicator that differentiate between what the light can or should be used for. For example, whether or not the light 138 corresponds to the x-ray field of the x-ray beam. In an aspect, the light source 136 is a multi-colored RGB LED. This light source 136 enables for the existing mirror system within the x-ray tube head 124 to still be utilized and allows for the light source 136 to change light type as required or desired. In an example, light type may be based at least partially on a change in color, and as such, the working light is a different color than the mapping light. In an aspect, the working light may be a white light, and the mapping light is a colored light. A colored light can be yellow so that illumination of the working area above the support platform 106 is still achieved. In other examples, the colored light can be red, orange, green, blue, indigo, violet, etc. as required or desired. Additionally, the colored light may be changed for different technologist so that color blindness does not affect the light differentiation. In other aspects, the mapping light may be a white light, while the working light is a colored light. In still other aspects, the mapping light and the working light may both be a different colored light. Furthermore, the light 138 can be adjustable in intensity as required or desired.

Additionally or alternatively, the light source 136 can be an incandescent lamp with filters, lasers, or the like that can produce different colored lights. In another example, the light source 136 can emit ultraviolet light and/or infrared light that can be used with additional imaging device(s) that are configured to make these light forms visible to the technologist. In yet other examples, a projector system may be used. All of these light sources can also provide light type differentiation to the technologist as described herein.

In still other examples, the types of light can be differentiated by patterns or audible sounds as required or desired. In certain aspects, a substantially similar light (e.g., white, yellow, blue, etc.) may be used for both the working light and the mapping light, one or both of the lights flashes at different speeds. In other aspects, the imaging system 100 may produce an audible sound when one or both of the working light and the mapping light are in use.

The light source 136 is configured to generate at least two different types of lights 138, and as such, the imaging system 100 is configured to monitor one or more conditions of its components so that the light source 136 can automatically change back and forth between light types. In the example, the imaging system 100 includes a tilt angle sensor 142 that measures and monitors the tilt angle of the x-ray tube head 124 relative to support platform 106. By monitoring the tilt angle of the x-ray tube head 124, the imaging system 100 can determine when the x-ray tube head 124 is titled relative to the support platform 106 such that the light 138 is no longer accurate with regards to the x-ray field of the x-ray beam. In some examples, the tilt angle sensor 142 may also measure and monitor the tilt angle of the support platform 106, because during some imaging procedures, the x-ray tube head 124 rotates in conjunction with the compression system 104. In an aspect, the sensor 142 may be that used for determining x-ray image angle for reconstruction in tomosynthesis imaging.

In the example, when the x-ray tube head 124 is tilted and moves away from the illustrated first position and being substantially orthogonal to the support platform 106, the imaging system 100 can automatically change the light 138 to the working light if the mapping light is being generated. Additionally, when the x-ray tube head 124 is oriented in the first position and substantially orthogonal to the support platform 106, the imaging system 100 can automatically change the light 138 to the mapping light if the working light is being generated. This change of the light 138 is based at least partially on a tilt angle of the x-ray tube head 124 relative to the support platform 106 and as measured and monitored by the sensor 142. In the example, the tilt angle of the x-ray tube head 124 is compared to a predetermined value to determine whether the tube head 124 is in the first position or not. In an aspect, the predetermined value may be between about 0°-±10°, which corresponds to the substantially orthogonal position and the acceptable accuracy of the mapping light. In another aspect, the predetermined value may be between about 0°-±5°. In yet another aspect, the predetermined value may be about 0°. As such, when the tilt angle of the x-ray tube head 124 is greater than the predetermined value, the working light is generated; otherwise when the tube head 124 is less than or equal to the predetermined value, the mapping light can be generated.

It should be appreciated that the x-ray tube head 124 can tilt to the left or right from the orthogonal first position. Thus, measuring the tilt angle of the tube head 124 can be both in the positive direction (e.g., tilting towards the right) and the negative direction (e.g., tilting towards the left), and relative to the 0° position. Additionally, smaller tilt angles (e.g., up to and including about ±10°) can still result in a relatively accurate image area 140 formed by the light 138. As such, the predetermined value may be within this range, and substantially orthogonal can include this accuracy range.

As described above, the change between the working light and the mapping light is based on tilt angle of the x-ray tube head 124. However, other component conditions of the imaging system 100 can be included in this determination of when to change between the working light and the mapping light. For example, the technologist typically uses the mapping light when the patient's breast is under at least some compression from the compression paddle 108. Immobilizing the patient's breast before confirming the x-ray field reduces the possibly of the patient's breast undesirability moving after positioning and prior to image acquisition. As such, to further increase performance of the light source 136, the change in light type can also be based on a compression force generated by the compression paddle 108. This further narrows the use of the mapping light for the technologists so that the mapping light is generated when it is actually needed during the breast positioning and compression process prior to image acquisition. Additionally, the light 138 also will not undesirably change back and forth during the breast positioning and compression procedures.

The imaging system 100 also includes a compression force sensor 144 that measures and monitors the compression force applied by the compression paddle 108 on the patient's breast. By monitoring the compression force of the compression paddle 108, the imaging system 100 can determine when the patient's breast is being compressed by the technologist so that once the technologist has immobilized the patient's breast and is ready for x-ray field confirmation, the light 138 will change to the mapping light from the working light.

In the example, when the compression paddle 108 generates a compressive force on the patient's breast, the imaging system 100 can automatically change the light 138 to a mapping light if a working light is being generated. Additionally, when the compression paddle 108 is not generating a compressive force on the patient's breast, the imaging system 100 can automatically change the light 138 to a working light if the mapping light is being generated. This change of the light 138 is based at least partially on a compression force generated by the compression paddle 108 and as measured and monitored by the sensor 144. In the example, the compression force of the compression paddle 108 is compared to a predetermined value to determine whether a compression for is present or not within the imaging system 100. In an aspect, the predetermined value may be between about 0-5 pounds. In another aspect, the predetermined value may be between about ½-5 pounds. As such, when the compression force is greater than the predetermined value, the mapping light can be generated; otherwise when the compression force of the compression paddle 108 is less than or equal to the predetermined value, the general working light is generated.

As described herein, two component conditions of the imaging system 100 are used to determine what type of light 138 is generated (e.g., tilt angle and compression force). It should be appreciated that any other condition of the imaging system 100 that can be sensed and/or monitored may additionally or alternatively be used in the determination of what type of light 138 is generated. In one example, paddle identification information that is read by the imaging system 100 can be used to determine what type of light 138 is generated. In this example, reading that a biopsy paddle is attached may be used to base the light type on. In other examples, sensing a biopsy device being attached to the imaging system 100 may be used to determine what type of light 138. Other conditions of the imaging system 100 are also contemplated herein.

Additionally, in the example, the type of light 138 being generated by the light source 136 is based on two different conditions of the imaging system 100. The tilt angle of the x-ray tube head 124 and the compression force of the compression paddle 108. Two conditions (e.g., the tube head 124 being substantially orthogonal to the support platform 106 and the compression paddle 108 generating a compression force) need to be satisfied so as to change the working light to the mapping light. However, as soon as one condition, either the tilt angle or the compression force, no longer satisfies the predetermined values, then the mapping light changes back to the working light. Exemplary flowcharts of how the type of light 138 is determined are illustrated in FIGS. 4 and 5 and described further below.

Figure 3:
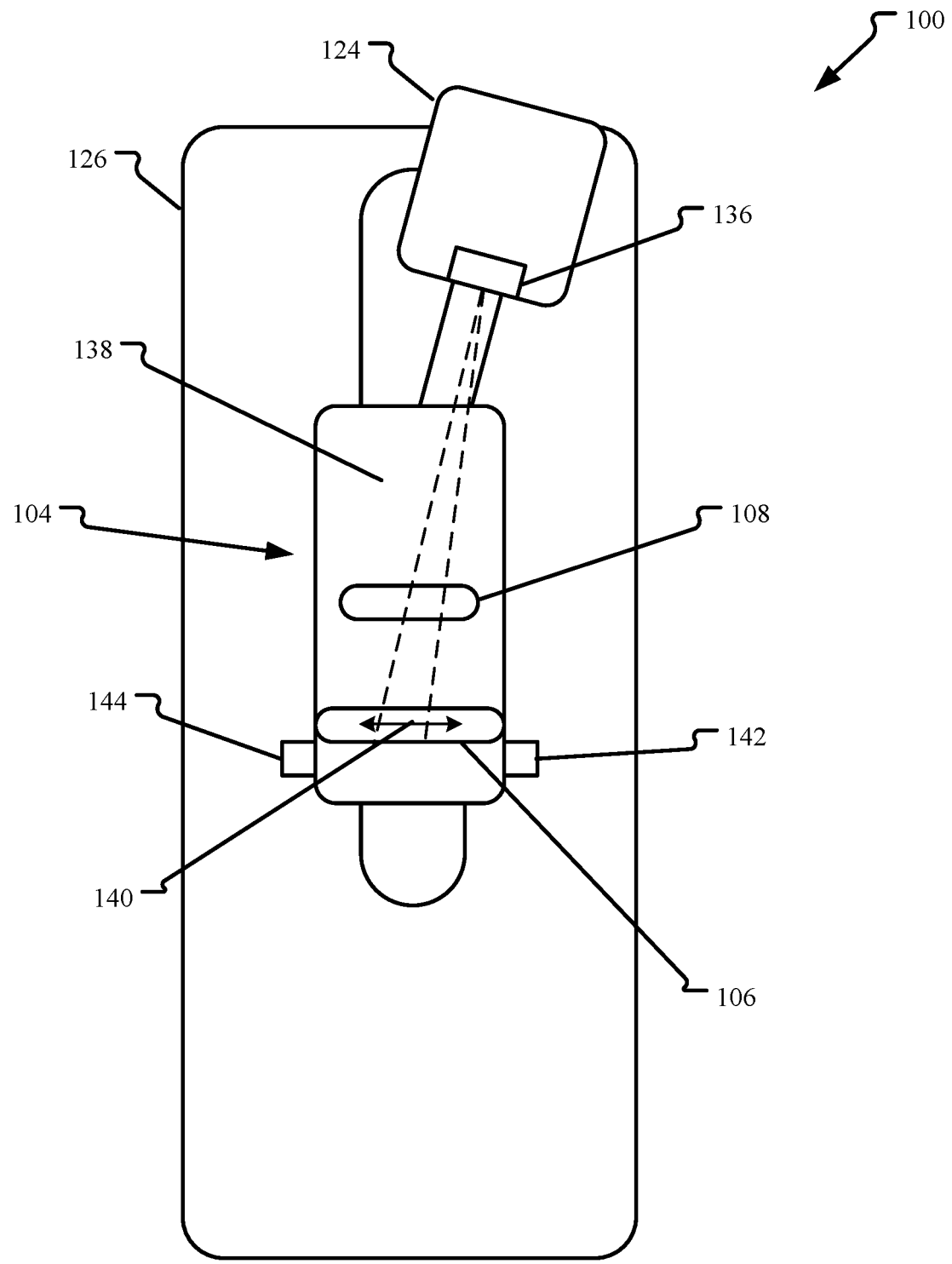
FIG. 3 is a schematic view of the light source shown in FIG. 2 and with the x-ray tube head in a second position.

FIG. 3 is a schematic view of the light source 136 and with the x-ray tube head 124 in a second position. Certain components are described above, and thus, are not necessarily described further. The second position is when the x-ray tube head 124 is moved away from being substantially orthogonal to the support platform 106 (as illustrated in FIG.

3). This tilting movement can be measured and monitored by the sensor 142. In the second position, the light source 136 still generates the light 138 that is directed towards the support platform 106, however, as described above, the light 138 is no longer accurate in regards to mapping the x-ray field of the x-ray source and the imaging area 140. In an example, the light 138 directed towards the support platform 106 is distorted due to the keystone effect because the platform is disposed at an angle relative to the light source 136. This distortion causes the light 138 to be in more of a trapezoidal shape in plan view (rather than a square shape) and with the right edge of the beam longer than the left edge because the tube head 124 is tilted towards the right (as illustrated in FIG. 3). This trapezoidal shape would be mirrored when the tube head 124 is tilted towards the left. As such, in the second position, the light 138 is the general working light, and will never change to the mapping light, no matter what the compression force is of the compression paddle 108. Similarly, when the compression paddle 108 is not generating a compression force as measured by the sensor 144, the light is the general working light, and will never change to the mapping light, no matter what the tilt angle of the tube head 124 is measured. As such, both the tilt angle and the compression force conditions have to be satisfied so as to change the working light to the mapping light. In the example, the working light is the baseline light type of the light 138.

Figure 4:
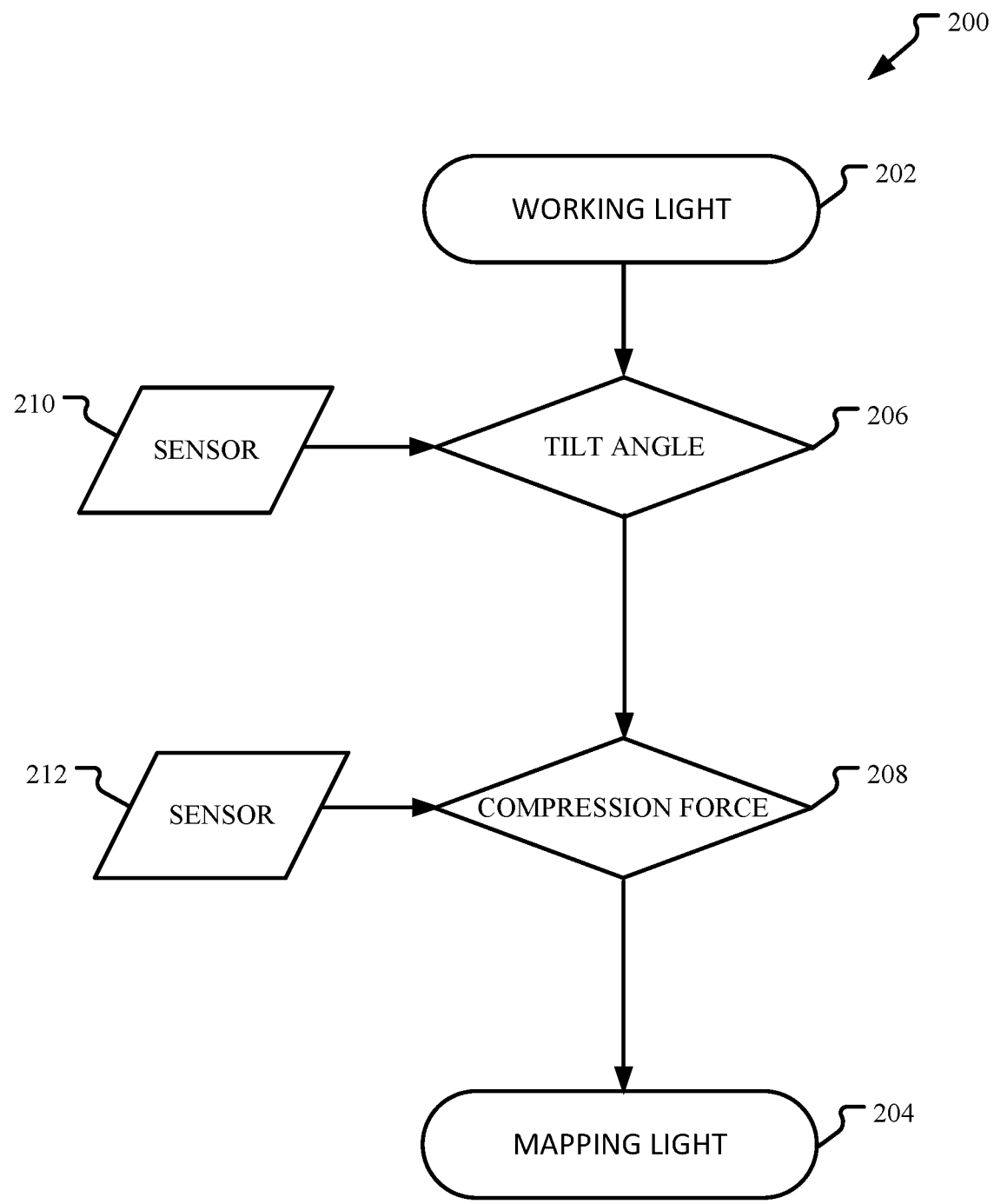
FIG. 4 depicts a flowchart illustrating changing a working light to a mapping light.
Figure 5:
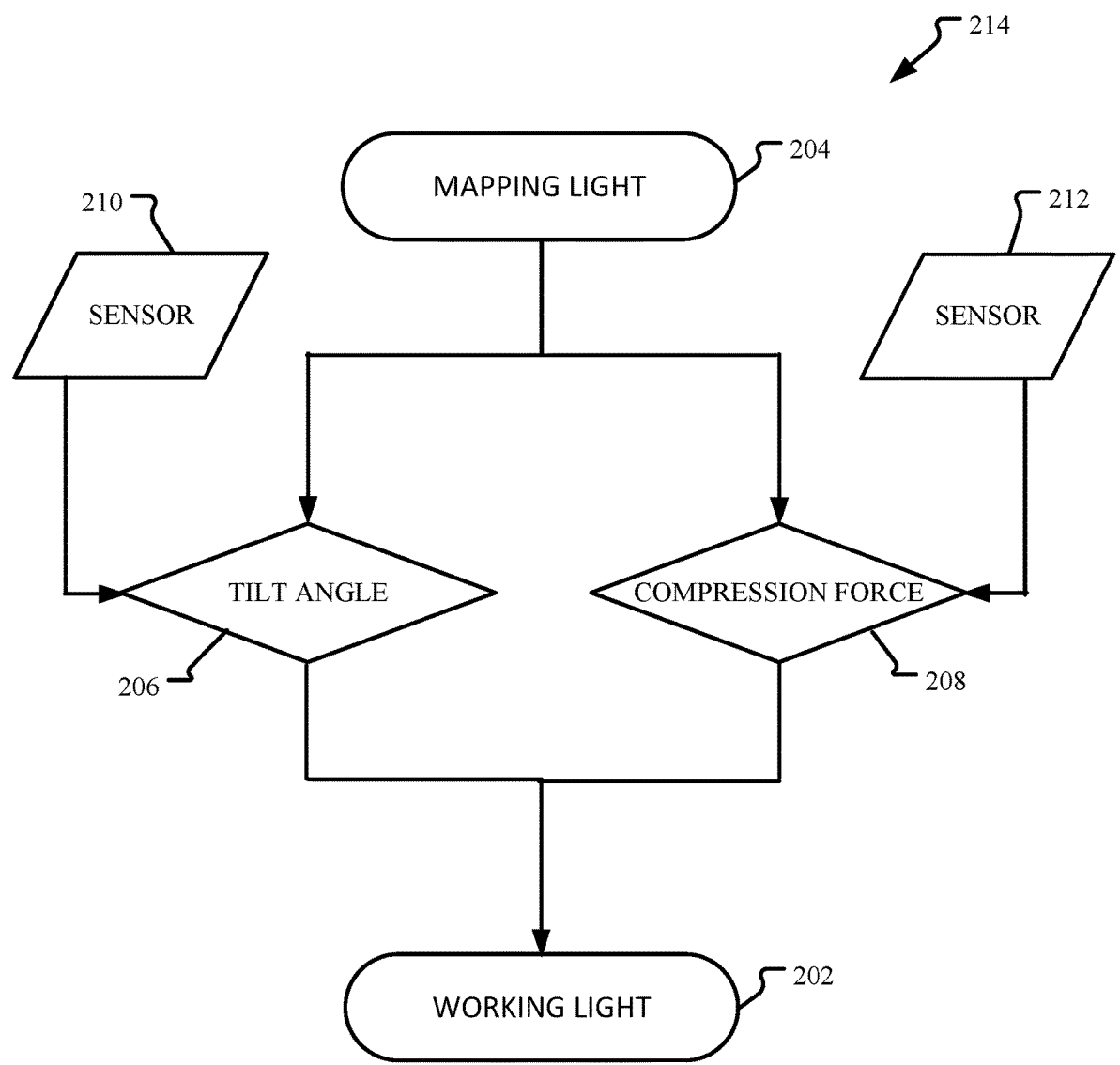
FIG. 5 depicts a flowchart illustrating changing a mapping light to a working light.

FIG. 4 depicts a flowchart 200 illustrating changing a working light 202 to a mapping light 204. To have the image system light change from the baseline of the working light 202 to the mapping light 204 for the technologist, both a tilt angle condition 206 and a compression force condition 208 need to be satisfied as described herein. Thus, the conditions 206, 208 are illustrated in series in the flowchart 200. If only one condition 206, 208 is satisfied, the working light 202 is maintained by the imaging system and the mapping light 204 is not generated. In the example, both conditions 206, 208 have input values measured from the imaging system by sensors 210, 212 that are used for monitoring and determining when the conditions 206, 208 are or are not satisfied. In contrast, FIG. 5 depicts a flowchart 214 illustrating changing the mapping light 204 to the working light 202. To have the image system light change or revert from the mapping light 204 to the working light 202, only one of the tilt angle condition 206 or the compression force condition 208 need to be satisfied as described herein. Thus, the conditions 206, 208 are illustrated in parallel in the flowchart 214. In the example, both conditions 206, 208 have input values measured from the imaging system by sensors 210, 212 that are used for monitoring and determining when the conditions 206, 208 are or are not satisfied. It should be appreciated that while FIGS. 4 and 5 illustrate the conditions 206, 208 being monitored by the imaging system are the tilt angle of the tube arm and the compression force of the compression paddle, any other component condition of the imaging system may be measured and monitored as required or desired.

Figure 6:
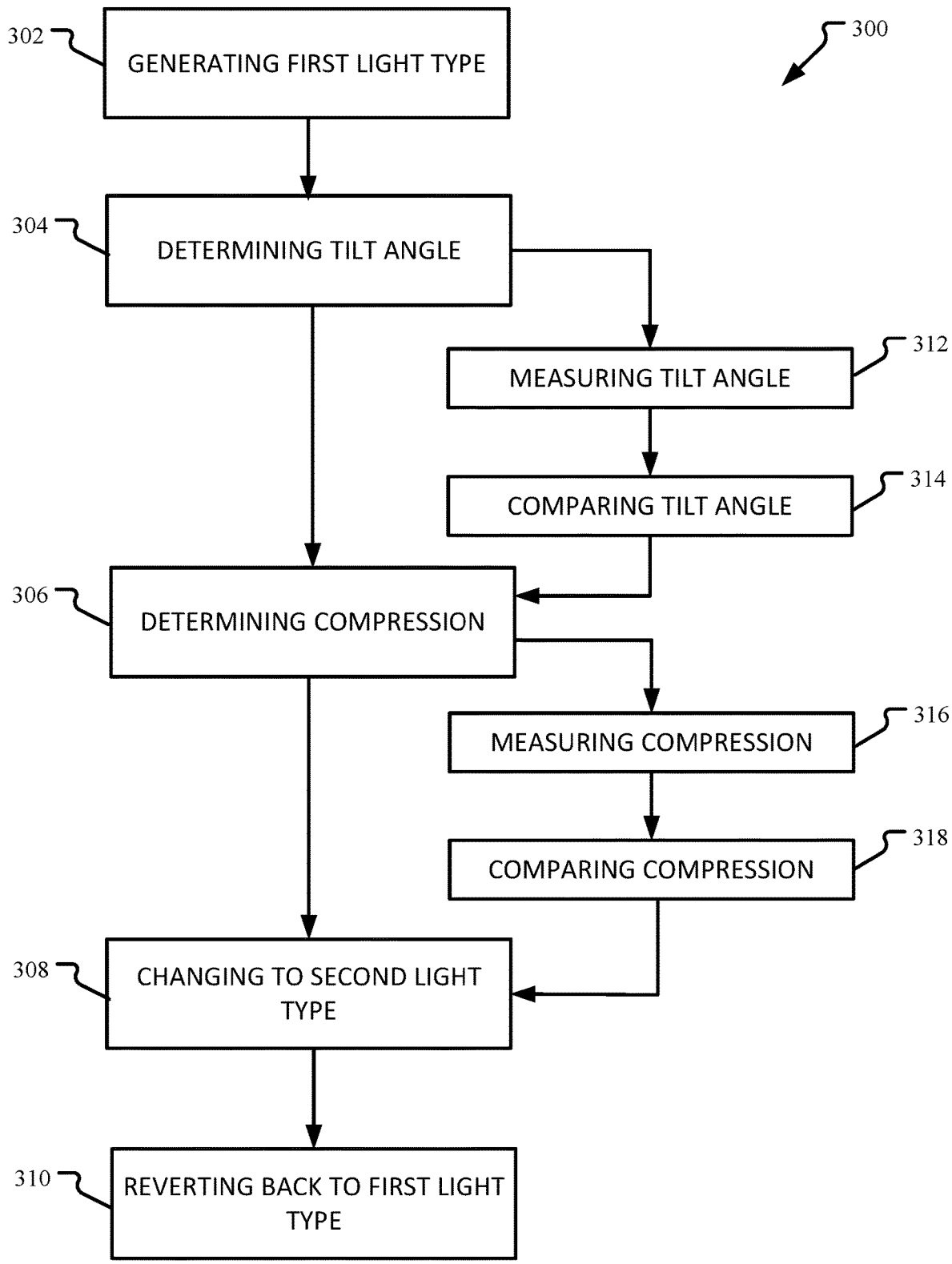
FIG. 6 depicts a flowchart illustrating a method of illuminating a support platform of an imaging system.

FIG. 6 depicts a flowchart illustrating a method 300 of illuminating a support platform of an imaging system. The imaging system can be the system described above in FIGS. 1A-3, and the illumination is differentiated based on one or more component conditions of the imaging system to increase breast positioning and compression efficiency for the technologist. Additionally, this differentiation of the illumination enables the technologist to more easily identify when they are able to rely on the light for mapping the x-ray field of the x-ray beam. The method 300 begins with generating a first light type by a light source (operation 302). The generated light type is directed toward a support platform for the benefit of the technologist.

The imaging system determines a tilt angle of the x-ray tube head (operation 304) and determines a compression force of the compression paddle (operation 306). Based on the determined tilt angle and the determined compression force, the first light type is selectively changed to a second light type generated by the light source (operation 308). In the example, the first light type is different than the second light type. In an aspect, the first light type is a different color than the second light type and the light source is a multi-colored LED. In some examples, the first light type is a white light and is considered a general working light for the technologist, and the second light type maps an x-ray field of an x-ray source of the x-ray tube head and is considered a mapping light. When a change in either the determined tilt angle or the determined compression force is detected by the imaging system, the light source reverts to the first light type (operation 310).

In some examples, determining the tilt angle of the x-ray tube head (operation 304) can include measuring the tilt angle relative to the support platform (operation 312) and comparing the measured tilt angle to a predetermined value (operation 314). When the measured tilt angle is less than or equal to the predetermined value, the first light type is changeable to the second light type, and when the measured tilt angle is greater than the predetermined value, the second light type changes to the first light type. In an aspect, the predetermined tilt angle value is between about 0°-±10° of the x-ray tube head relative to the support platform.

In other examples, determining the compression force (operation 306) can include measuring the compression force applied by the compression paddle to a patient's breast (operation 316) and comparing the measured compression force to a predetermined value (operation 318). When the measured compression force is less than or equal to the predetermined value, the first light type is changeable to the second light type, and when the measured compression force is greater than the predetermined value, the second light type changes to the first light type. In an aspect, the predetermined compression force value is between about 0-5 pounds.

Figure 7:
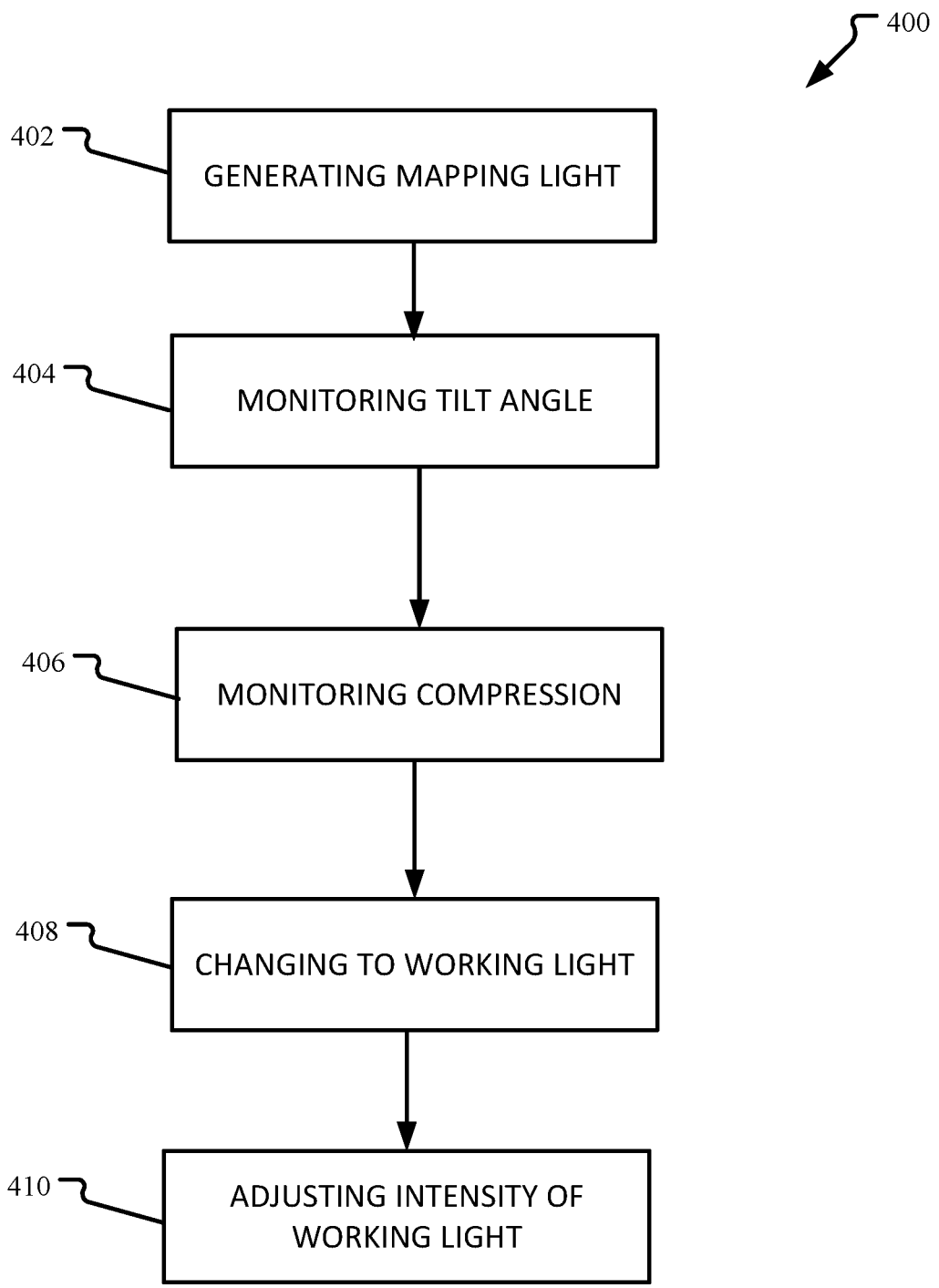
FIG. 7 depicts a flowchart illustrating another method of illuminating a support platform of an imaging system.

FIG. 7 depicts a flowchart illustrating another method 400 of illuminating a support platform of an imaging system. The imaging system can be the system described above in FIGS. 1A-3, and the illumination is differentiated based on one or more component conditions of the imaging system to increase breast positioning and compression efficiency for the technologist. The method 400 begins with generating, via a light source, a mapping light directed towards the support platform (operation 402). The mapping light is based on an x-ray tube head being at a substantially orthogonal position relative to the support platform and a compression paddle generating a compression force on a patient's breast. The mapping light also corresponds to an x-ray field of the x-ray source.

The imaging system monitors a tilt angle of the x-ray tube head relative to the support platform (operation 404) and monitors the compression force of the compression paddle (operation 406). Based on the tilt angle of the x-ray tube moving away from the substantially orthogonal position or the compression force being less than or equal to a predetermined value, the mapping light generated by the light source is changed to a working light (operation 408). In the example, the mapping light is a different color than the working light and the light source is a multi-colored LED.

In an aspect, the working light can be a white light. In some example, the method 400 can include adjusting the intensity of the working light (operation 410). By adjusting the intensity of the working light, the technologist can make the patient more comfortable while still enabling illumination for the breast positioning and compression procedures.

Figure 8:
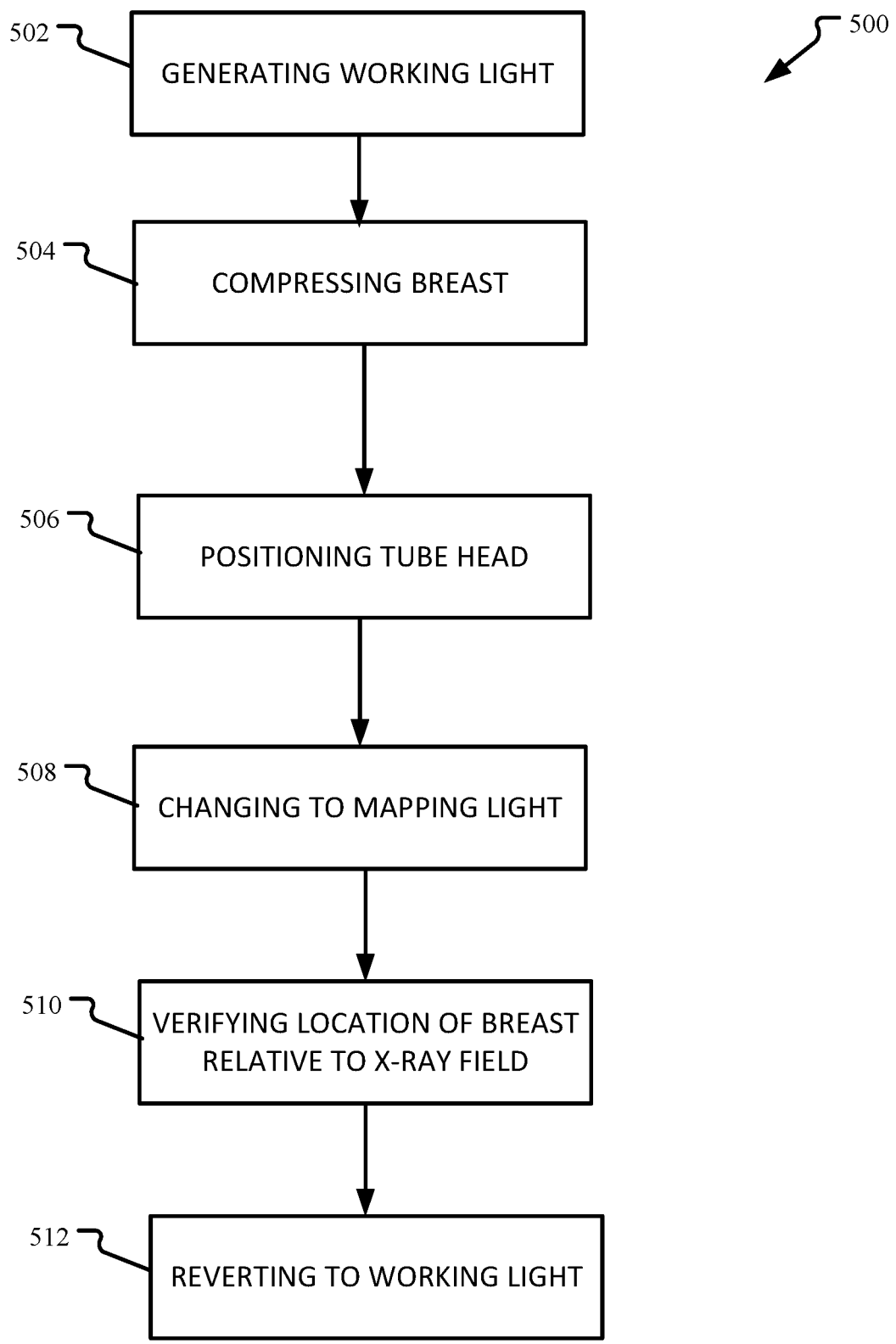
FIG. 8 depicts a flowchart illustrating a method of compressing a patient's breast on an imaging system.

FIG. 8 depicts a flowchart illustrating a method 500 of compressing a patient's breast on an imaging system. The imaging system can be the system described above in FIGS. 1A-3. The method 500 begins with generating a working light directed towards a support platform via a light source (operation 502). The patient's breast is compressed between a compression paddle and the support platform (operation 504). The compression paddle induces a compression of the patient's breast for immobilization. After compression of the patient's breast, an x-ray tube head is positioned substantially orthogonal relative to the support platform (operation 506). Based on the position of the x-ray tube head and the compression force of the compression paddle, the working light generated by the light source is changed to a mapping light (operation 508). The mapping light can then be used to verify that the patient's breast is located within an x-ray field of the x-ray source (operation 510).

In some examples, after the working light is changed to the mapping light, the light source automatically reverts to the working light (operation 512). Reverting back to the working light can occur when the patient's breast is released from compression or when the x-ray tube head is tilted away from the substantially orthogonal position.

This disclosure describes some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art. Any number of the features of the different examples described herein may be combined into one single example and alternate examples having fewer than or more than all of the features herein described are possible. It is to be understood that terminology employed herein is used for the purpose of describing particular examples only and is not intended to be limiting. It must be noted that, as used in this specification, the singular forms "a," "an," and "the" include plural referents unless the context clearly dictates otherwise.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

What is claimed is:

1. An imaging system comprising:
a gantry;
an immobilization system coupled to the gantry and rotatable relative to the gantry, wherein the immobilization system comprises a paddle, a support platform, and an x-ray receptor; and
an x-ray tube head coupled to the gantry and comprising an x-ray source and a light source, wherein the x-ray tube head is independently rotatable relative to the gantry and the immobilization system,
wherein the imaging system is operable in at least a first imaging mode and a second imaging mode, wherein the light source is configured to generate at least a first light type and a different second light type directed towards the support platform for immobilization of a breast at the immobilization system, the first light type based on the imaging system being in the first imaging mode and the second light type based on the imaging system being in the second imaging mode.

2. The imaging system of claim 1, wherein the first imaging mode is defined by the x-ray tube head being at a 0° tube head angle position relative to the support platform.

3. The imaging system of claim 2, wherein the second imaging mode is defined by the x-ray tube head being tilted away from the 0° tube head angle position relative to the support platform.

4. The imaging system of claim 2, wherein the first imaging mode is also defined by a compression force generated by the paddle.

5. The imaging system of claim 1, wherein the first imaging mode is a mammography mode.

6. The imaging system of claim 5, wherein the second imaging mode is a tomosynthesis mode.

7. The imaging system of claim 1, wherein the second imaging mode is a biopsy mode.

8. The imaging system of claim 7, wherein the biopsy mode is based on a biopsy device attached to the imaging system.

9. The imaging system of claim 7, wherein the biopsy mode is based on a biopsy paddle attached to the imaging system.

10. The imaging system of claim 1, wherein the light source is a multi-colored light emitting diode.

11. The imaging system of claim 1, wherein the imaging system is a multi-modal imaging system.

12. A method of illuminating a support platform of an imaging system, the imaging system comprising: (a) a gantry, (b) an immobilization system comprising a paddle, the support platform, and an x-ray receptor, the immobilization system rotatable relative to the gantry, and (c) an x-ray tube head comprising an x-ray source and a light source, and independently rotatable relative to the gantry and the immobilization system, the method comprising:
positioning the imaging system in a first imaging mode,
generating, via the light source, a first light type directed towards the support platform based on the imaging system being in the first imaging mode, wherein the first light type is for immobilization of a breast at the immobilization system;
changing the first light type to a second light type generated by the light source based on the imaging system changing to a second imaging mode, wherein the first light type is different than the second light type.

13. The method of claim 12, wherein positioning the imaging system in the first imaging mode includes positioning the x-ray tube head at a 0° tube head angle position relative to the support platform.

14. The method of claim 13, wherein changing to the second imaging mode includes moving the x-ray tube head away from the 0° tube head angle position relative to the support platform.

15. The method of claim 13, wherein positioning the imaging system in the first imaging mode also includes generating a compression force via the paddle.

16. The method of claim 12, wherein positioning the imaging system in the first imaging mode including positioning the imaging system in a mammography mode.

17. The method of claim 16, wherein changing to the second imaging mode includes positioning the imaging system in a tomosynthesis mode.

18. The method of claim 12, wherein changing to the second imaging mode includes determining a biopsy device is attached to the imaging system.

19. The method of claim 12, wherein changing to the second imaging mode includes determining a biopsy paddle is attached to the imaging system.

20. The method of claim 12, wherein changing the first light type to the second light type includes changing light colors.

\* \* \* \* \*